US005728090A

United States Patent [19]

Martin et al.

[11] Patent Number: 5,728,090
[45] Date of Patent: Mar. 17, 1998

[54] APPARATUS FOR IRRADIATING LIVING CELLS

[75] Inventors: Todd S. Martin; Ronald W. Ignatius, both of Dodgeville, Wis.

[73] Assignee: Quantum Devices, Inc., Barneveld, Wis.

[21] Appl. No.: 385,771

[22] Filed: Feb. 9, 1995

[51] Int. Cl.⁶ .................. A61F 2/38; A61B 17/36
[52] U.S. Cl. ................. 606/3; 606/2; 606/11; 606/14; 607/1
[58] Field of Search ..................... 606/1–3, 7–9, 606/10–16, 27; 607/1, 88–95

[56] References Cited

U.S. PATENT DOCUMENTS

| | | | |
|---|---|---|---|
| 4,336,809 | 6/1982 | Clark | 128/665 |
| 4,614,190 | 9/1986 | Stanco et al. | 128/395 |
| 4,822,335 | 4/1989 | Kawai et al. | |
| 4,886,831 | 12/1989 | Morcos et al. | |
| 4,889,129 | 12/1989 | Dougherty et al. | 128/664 |
| 4,932,934 | 6/1990 | Dougherty et al. | |
| 4,957,481 | 9/1990 | Gatenby | |
| 5,053,033 | 10/1991 | Clarke | 606/3 |
| 5,054,867 | 10/1991 | Wagnieres et al. | 385/31 |
| 5,146,917 | 9/1992 | Wagniéres et al. | |
| 5,151,096 | 9/1992 | Khoury | |
| 5,163,898 | 11/1992 | Morcos et al. | |
| 5,257,970 | 11/1993 | Dougherty | 604/20 |
| 5,278,432 | 1/1994 | Ignatius et al. | 257/88 |
| 5,298,018 | 3/1994 | Narciso, Jr. | |
| 5,401,270 | 3/1995 | Müller et al. | |
| 5,445,608 | 8/1995 | Chen et al. | |
| 5,454,794 | 10/1995 | Narciso et al. | |

OTHER PUBLICATIONS

Whelan, Henry T. et al., schematic diagram of laser–fiber optic catheter for PDT, Milwaukee, WI, 1993 or earlier.
Whelan, Henry T. et al., "The Role of Photodynamic Therapy in Posterior Fossa Brain Tumors," *J Neurosurg* 79:562–568, Oct. 1993, pp. 562–568.
Whelan, Henry T. et al., "Interactions of Merocyanine 540 with Human Brain Tumor Cells," *Pediatric Neurology*, vol. 8, No. 2 Mar.–Apr. 1992, pp. 117–120.
Schlager, Kenneth J. et al., "An LED–Array Light Source for Medical Therapy," paper presented at Biomedical Optics '93, Jan. 16–22, 1993.
Schlager, Kenneth J., "Immunophototherapy for the Treatment of AIDS and AIDS–related Infections," paper, published in Jan., 1993.
Lytle, Charles A., et al., "Light Emitting Diode Source for Photodynamic Therapy," *SPIE* vol. 1881 Optical Methods for Tumor Treatment and Detection, pp. 180–188, 1993.
Schlager, et al., "LED Arrays and Photodynamic Therapy: A Progress Report," *SPIE* vol. 2131, pp. 341–353, 1994.
Wilson, D.C. et al., "Instrumentation and Light Dosimetry for Intra–operative Photodynamic Therapy (PDT) of Malignant Brain Tumors," *Phys. Med Biol.*, 1986 vol. 31, No. 2, pp. 125–133.
Schlager, Kenneth J. et al., "Immunotherapy for the Treatment of Cancer of the Larynx," *SPIE* vol. 1881, pp. 148–158, 1993.

*Primary Examiner*—Jennifer Bahr
*Assistant Examiner*—Stephen Huang
*Attorney, Agent, or Firm*—Michael, Best & Friedrich

[57] ABSTRACT

Apparatus for use in photodynamic therapy (PDT) is provided having a substantially cylindrical support to which is attached a removable, multi-sided head. Each side of the head has an array of light-emitting diodes that provide monochromatic light to activate a photosensitive dye. The apparatus may be used in invasive surgery to treat brain tumors and the like. The apparatus may be used for topical treatments by providing a removable reflector over the light-emitting head. The temperature of the head is controlled, and the head is cooled by circulating cooling fluid through the head. The use of the cooling fluid allows the LEDs to be driven beyond their rated capacity. The catheter may also include an expandable light diffuser that is affixed over the light-emitting head and that is filled with a diffuser fluid such as a lipid solution. The apparatus may also be used to provide radiant energy to plants or to patients in non-PDT applications.

18 Claims, 5 Drawing Sheets

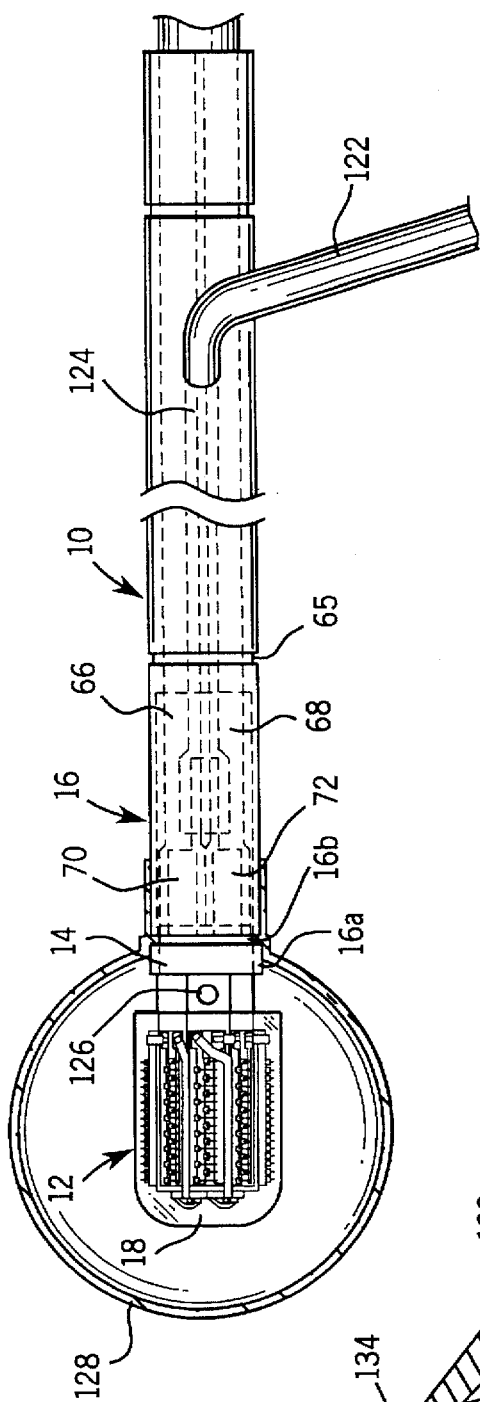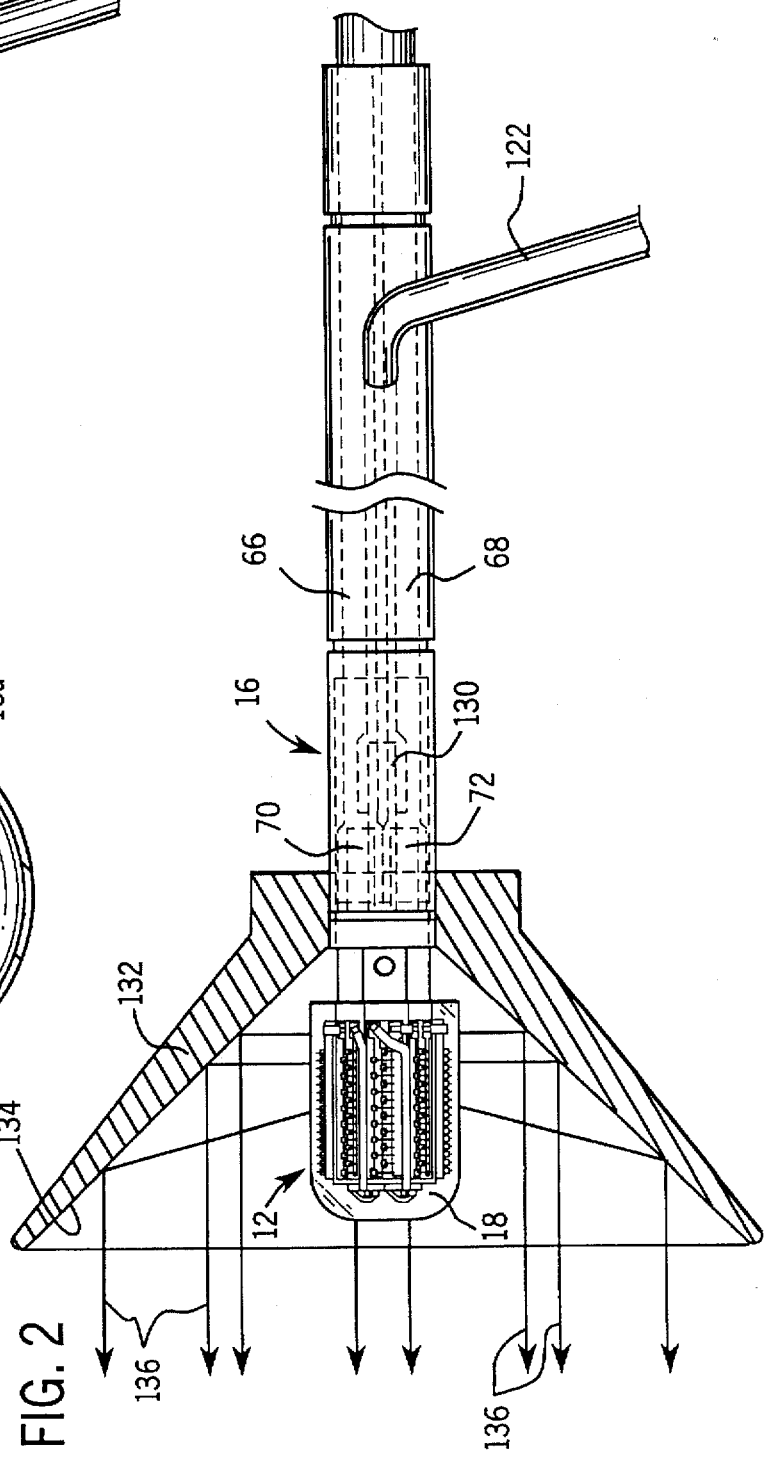

APPARATUS FOR IRRADIATING LIVING CELLS

BACKGROUND OF THE INVENTION

This invention relates to devices used for irradiating a patient or other living cells. More particularly, this invention relates to a catheter for photodynamic therapy used to treat tumors and to destroy microbes.

Photodynamic therapy (PDT) is being increasingly used to treat tumors, skin lesions and the like. When PDT is used to treat malignant tumors, a photosensitive dye is injected into the patient at least 24 hours before the planned therapy. The photosensitive dye is typically a hematoporphyrin derivative that is retained in malignant tissue. These dyes absorb light at wavelengths which penetrate cancerous tissue to produce singlet oxygen in vivo that destroys microbes and malignant cells.

It is necessary to deliver a large amount of light radiation to the tumor at specific wavelengths to activate the photosensitive dye. Most photosensitive dyes are activated at wavelengths between about 300 nanometers and 800 nanometers. However, it is know that greater penetration of the tumor occurs at higher wavelengths, up to about 1300 nanometers.

Typical prior art PDT light delivery systems have used monochromatic lasers in combination with fiber optic catheters. One such light deliver system is disclosed in U.S. Pat. No. 4,889,129 issued Dec. 26, 1989 to Dougherty et al. In such typical prior art systems, a laser provides monochromatic light to a fiber optic cable, which in turn transmits the light through a light diffuser to the tumor.

Such prior art devices have certain disadvantages. First, they are complicated and expensive since they require a laser source, electronic controls, and a fiber optic catheter.

A second disadvantage is that such prior art systems are inefficient. A typical fiber optic catheter transmits only about 30% to 50% of available light energy. Additional energy losses occur in the diffuser which surrounds the light-emitting end of the catheter and diffuses the light from the catheter. The blood and the surrounding tissue also attenuate a substantial portion of the input power. The net result is that only about 25% to 30% of the power is available to activate the photosensitive dye. Thus, a laser light source having an input of two watts yields about one watt at the catheter output and 0.4 watts/cm$^2$ to the photosensitized tissue. A discussion of these power losses is found in U.S. Pat. No. 5,298,018 issued Mar. 29, 1994 to Narciso, Jr.

Besides increasing the required size and cost of the light source, these energy losses also reduce the effectiveness of the treatment since the depth of radiation penetration into the tissue is reduced. With reduced penetration, surgical techniques are required to remove much of the malignant tissue before photodynamic therapy commences, and the likelihood that all malignant tissue is destroyed is lessened.

Arrays of light emitting diodes (LEDs) have been used in photodynamic therapy to typically treat skin lesions, larynx cancer, and dermatological conditions. See "An LED-Array Light Source for Medical Therapy," Kenneth J. Schlager and Ronald W. Ignatius, SPIE Vol. 1892 *Medical Lasers and Systems II*, January 1993. However, the use of such LED arrays has been limited to cutaneous applications.

SUMMARY OF THE INVENTION

Apparatus is disclosed for providing radiant energy to a patient for the purpose of photodynamic therapy (PDT), to otherwise irradiate a patient, or to irradiate other living plant or animal cells. The apparatus includes a support member, preferably made of surgical steel, having a proximal end and a radiation transmitting head removably connected to the proximal end. The head includes at least two sides, and preferably eight sides and an end face, each of which has a plurality of optoelectronic devices thereon. Each of the plurality of optoelectronic devices is preferably an array of light-emitting diodes (LEDs).

The head is preferably removable, and may be fitted with a removable reflector for topical treatments, or with an expandable light diffuser. If a light diffuser is used, the apparatus includes a means for supplying a fluid to the diffuser, including a fluid passageway that receives the fluid, an inlet end, and an outlet near the proximal end of the wand member.

The apparatus also preferably includes a means for limiting the temperature of the head, that includes a first passageway in the support member that receives and carries a cooling fluid to the head, and a second passageway in the support member that carries the cooling fluid away from the head. The temperature-limiting means also includes a temperature sensor that senses the temperature of the head, and a means for reducing or terminating the power to the optoelectronic devices if the head temperature exceeds a set level. A continuously-variable power source may be used to adjust the power output of the optoelectronic devices as well.

In one embodiment, the support member and the radiation transmitting head together comprise a catheter that is used in invasive surgical procedures, such as the treatment of malignant brain tumors. In any case, the head preferably outputs substantially monochromatic light having a wavelength of between 300 to 1300 nanometers.

It is a feature and advantage of the present invention to provide an apparatus for photodynamic therapy that may be used during invasive surgical procedures.

It is yet another feature and advantage of the present invention to provide an apparatus for irradiating a patient that outputs substantially monochromatic light energy without the use of expensive lasers.

It is yet another feature and advantage of the present invention to provide an apparatus for use in photodynamic therapy that substantially reduces the energy losses typical of laser and fiber optic light delivery systems.

It is yet another feature and advantage of the present invention to provide an apparatus that may be used in a wide variety of invasive and non-invasive procedures in which living cells are irradiated.

These and other features and advantages of the present invention will be apparent to those skilled in the art from the following detailed description of the preferred embodiment and the drawings.

BRIEF DESCRIPTION OF THE DRAWINGS

FIG. 1 is a side view depicting a catheter according to the present invention having a removable light diffuser.

FIG. 2 is a side view depicting a head-support assembly with a removable reflector.

BRIEF DESCRIPTION OF THE PREFERRED EMBODIMENT

Figure 3:
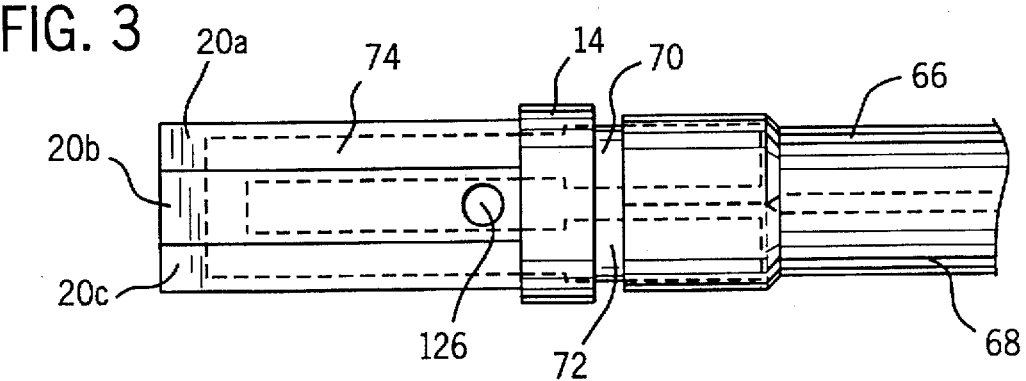
FIG. 3 is a side view of the head substrate-support assembly depicting the cooling fluid passageways.

FIG. 1 is a side view of a head-support assembly 10 that is used in the present invention. In FIG. 1, head 12 has a surgical steel shoulder 14 onto which a surgical steel support member 16 is press-fit. Head 12 is enclosed in a layer 18 of a transparent epoxy resin.

Figure 4:
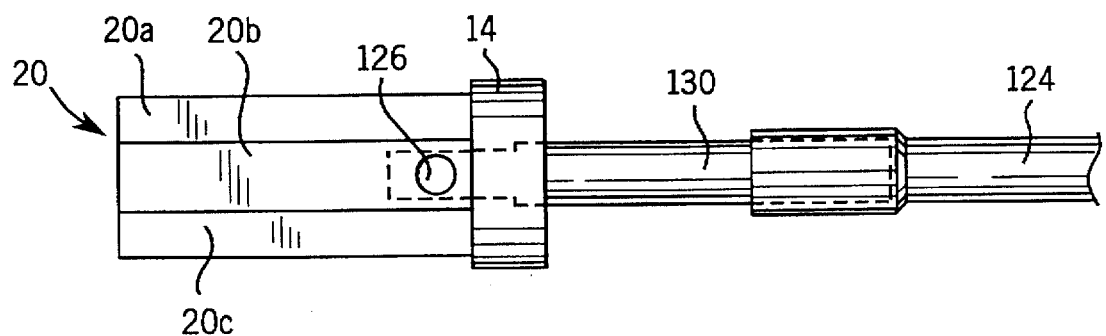
FIG. 4 is a side view of the head substrate depicting the fluid passageway for filling the expandable light diffuser.

Head 12 includes a substantially closed substrate 20 (FIGS. 3 through 6) that has a plurality of side faces and an end face. In the embodiment depicted and described herein, head 12 has eight side faces and one end face; however, a different number of side faces and end faces may be used. FIGS. 3 and 4 depict three side faces 20a, 20b, and 20c.

Figure 7:
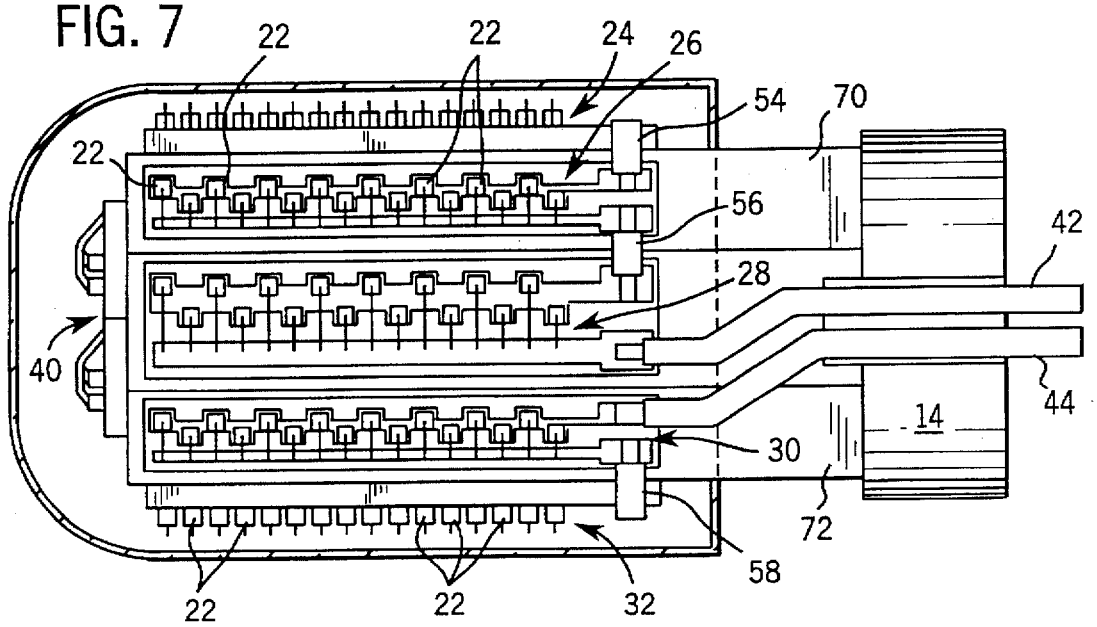
FIG. 7 is a first side view of a light-emitting head according to the present invention.
Figure 8:
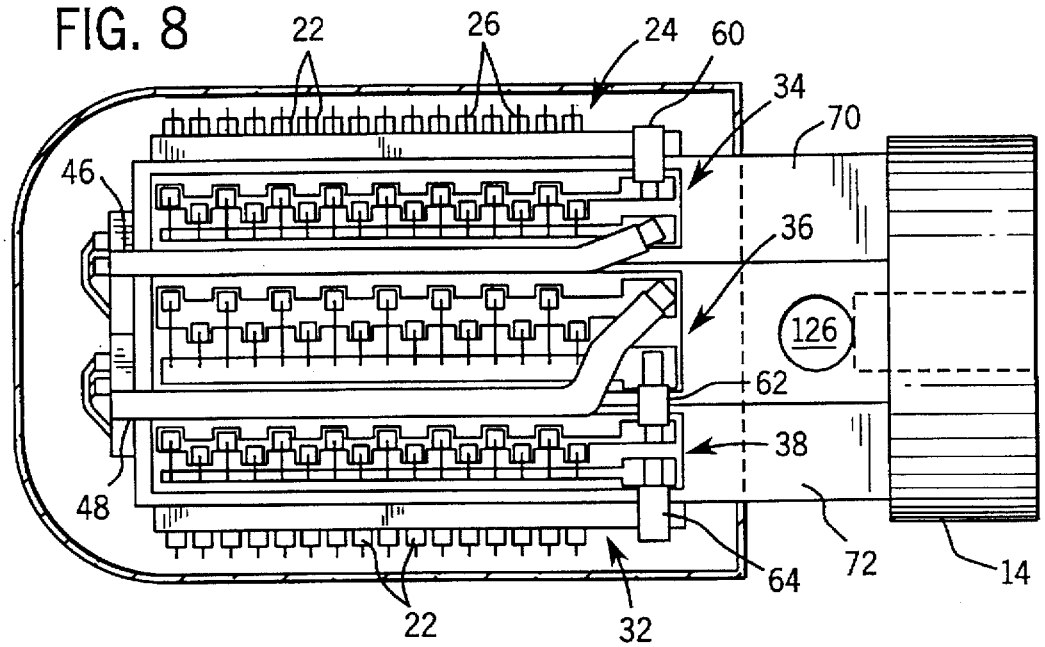
FIG. 8 is a side view from the opposite side of the light-emitting head.
Figure 9:
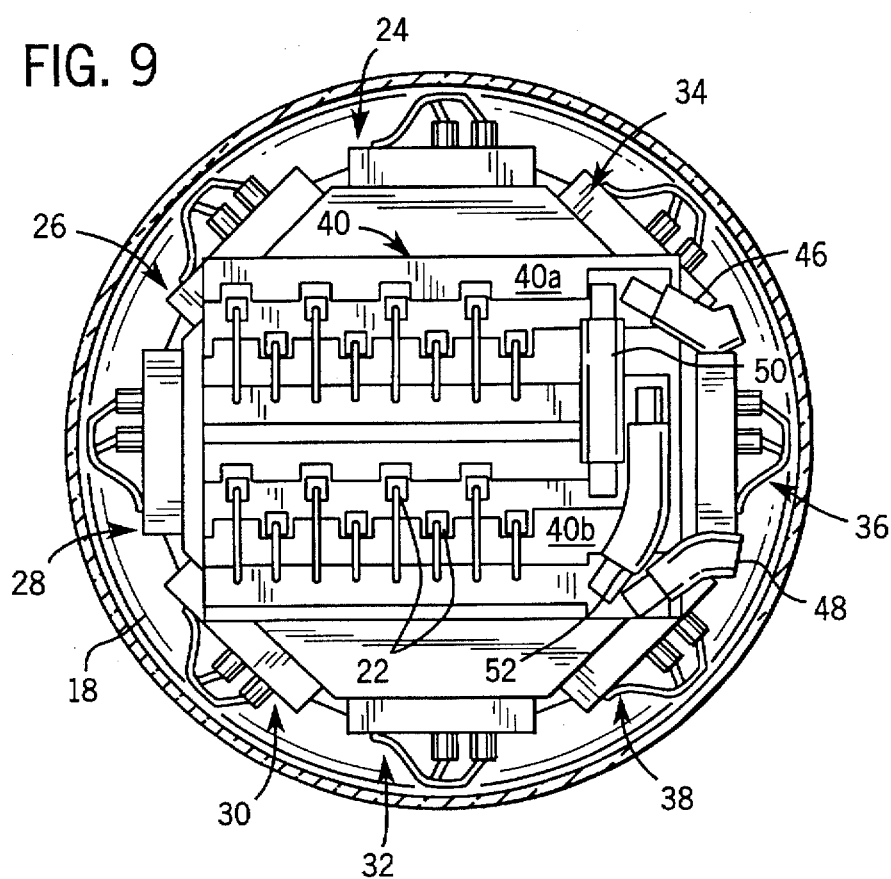
FIG. 9 is an end view of the light-emitting head.

Each of the side faces and the end face preferably has an array of optoelectronic devices disposed thereon. FIGS. 7 through 9 best depict these arrays of optoelectronic devices. The optoelectronic devices are preferably substantially monochromatic, double heterojunction Gallium Aluminum Arsenide light-emitting diodes of the type manufactured by Mitsubishi Kaisi Polytech of Japan, and are available from Showa Denkoa or Stanley, both of Japan, or from Hewlett-Packard of Palo Alto, Calif. The optoelectronic devices are connected together in a manner described in U.S. Pat. No. 5,278,432, issued Jan. 11, 1994 to Ignatius, et al., which is incorporated by reference herein.

In FIGS. 7 through 9, each of the side faces and the end face of head 12 has an array of sixteen parallel-connected optoelectronic devices 22. The use of electrically-powered optoelectronic devices instead of a laser-fiber optic apparatus substantially reduces power losses and equipment cost.

FIG. 7 depicts arrays 24, 26, 28, 30, and 32. FIG. 8 depicts arrays 34, 36 and 38 disposed on three additional side faces of the head. FIG. 9 depicts an array 40 disposed on the end face. Array 40 has two subarrays 40a and 40b which are connected in parallel.

Each of arrays 24 through 40 consists of 16 parallel-connected optoelectronic devices, with the arrays themselves connected in series. This arrangement minimizes the voltage required for the arrays while also allowing high input currents and providing high light energy output.

Each of the arrays is formed on a ceramic substrate, as disclosed in the above-referenced U.S. Pat. No. 5,278,432 to Ignatius et al.

Power is provided to arrays 24 through 40 by insulated wires 42 and 44. Wires 46 and 48 provide power to subarrays 40a and 40b, respectively. Subarrays 40a and 40b are connected together by insulated wires 50 and 52. Arrays 24 and 26 are connected together by an insulated wire 54 (FIG. 7). Arrays 26 and 28 are connected in series by an insulated wire 56. Arrays 30 and 32 are connected in series by an insulated wire 58. In FIG. 8, arrays 24 and 34 are connected together by an insulated wire 60. Arrays 36 and 38 are connected in series by an insulated wire 62. Finally, arrays 38 and 32 are connected in series by an insulated wire 64.

Referring again to FIGS. 1 and 2, support member 16 includes a substantially cylindrical, rigid, elongated member that is suitable to be held by the physician during patient therapy. Rib 65 may be used for gripping support member 16. Support member 16 is preferably a hollow tube having sufficient space inside thereof to enclose a first tubular passageway 66 that receives and carries a cooling fluid, such as saline, into head 12. The use of the cooling fluid and the thermoelectric cooler allows the LEDs to be driven up to ten times beyond their rated capacity. Support member 16 also includes a second passageway 68 that carries a cooling fluid away from head 12. Passageways 66 and 68 are best shown in FIG. 3.

As also shown in FIG. 3, passageway 66 is press-fit onto a tubular member 70 formed integral with head 12. Likewise, passageway 68 is press-fit onto a tubular member 72 formed integral with the head.

Figure 5:
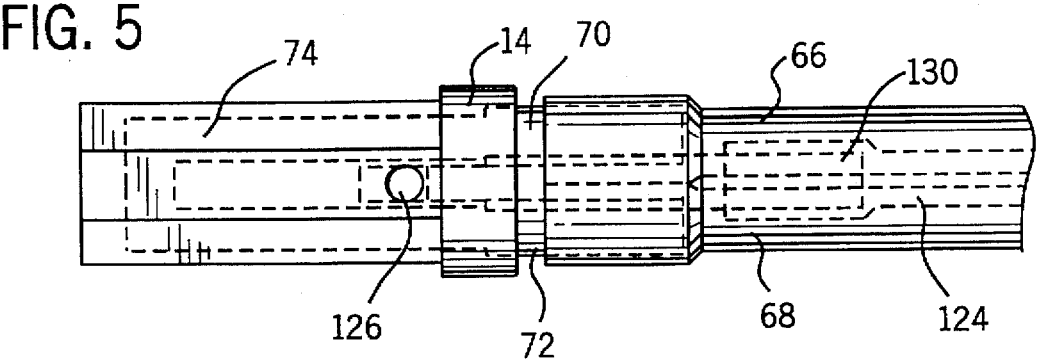
FIG. 5 is a side view of the head substrate-support assembly depicting both the cooling fluid passageways and the diffuser fluid passageway.
Figure 6:
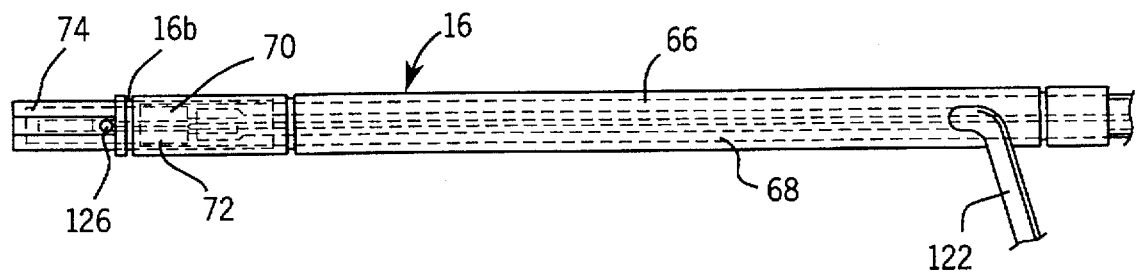
FIG. 6 is a side view depicting the head-support assembly, the optoelectronic devices having been removed.

As best shown in FIGS. 3, 5 and 6, head 12 includes a passageway 74 that receives cooling fluid from passageway 66 and tube 70 and that transmits the cooling fluid to tubular member 72 and passageway 68.

Figure 10:
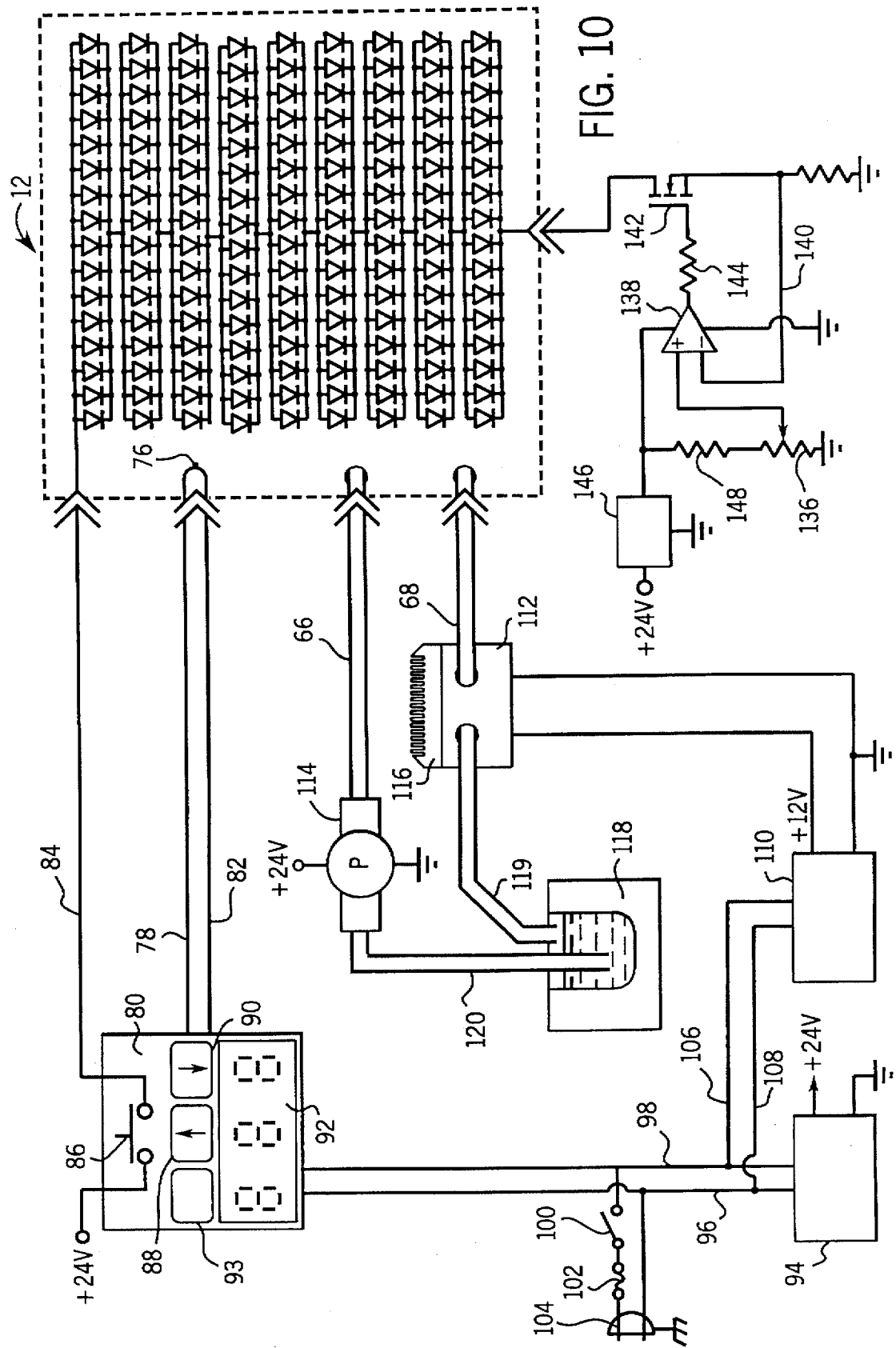
FIG. 10 is schematic diagram of the present invention.

The means by which the temperature of the head is controlled and the means by which the cooling fluid is pumped are best understood in connection with FIG. 10. In FIG. 10, head 12 includes a thermocouple 76 that is used to sense the temperature of the head. Thermocouple 76 is powered by current on a line 78 connected to a temperature indicator/controller 80, and provides a signal on line 82 to controller 80. One suitable controller is manufactured by Omega of Stamford, Conn., model no CN900. If the temperature of the head exceeds a preset level such as 96° Fahrenheit, power on line 84 is interrupted by opening an interrupt switch 86 in controller 80. The set point temperature may be raised by pushing button 88, or it may be lowered by pushing button 90. The set point temperature is displayed on a display 92 of controller 80 when set point button 93 is pushed; otherwise, the current temperature of head 12 is displayed on display 92. Controller 80 is powered by a 24-volt power source 94. One suitable power source is made by Toko America, Inc., model no. SW100-24F.

AC line current is provided to power supply 94 via lines 96 and 98 through an on/off switch 100, a fuse 102, and a grounded plug 104. AC line current is also provided via lines 106 and 108 to a 12-volt power supply 110 that is used to power a liquid-to-air thermoelectric cooler 112. A suitable 12-volt power supply is made by Toko America, Inc., model no. SW100-12F. A suitable thermoelectric cooler is made by Cool Corp., Gothenburg, Sweden, model no. LA-050-12-02. AC line current is provided to controller 80 via lines 96 and 98.

Cooling fluid is pumped to head 12 via a pump 114, which pumps the fluid through passageway 66. A suitable pump and motor assembly is made by Micropump Corp. of Concord, Calif., model nos. MCP 040 and MCP 332. The heated fluid is returned through passageway 68 into cooler 112, which includes a heat sink 116. The fluid is then returned to a water reservoir 118 via passageway 119. Pump 114 draws fluid from reservoir 118 via passageway 120.

The present invention also includes a means for providing a diffuser fluid to head 12, as well as a removable, expandable light diffuser that is detachably affixed over head 12.

As best shown in FIG. 1, a diffuser fluid, which may be a lipid solution, is provided to support member 16 via a tube 122 that is interconnected with a passageway 124 within support member 16. Passageway 124 has an outlet 126 near proximal end 16a of support member 16. Also disposed near proximal end 16a is a rib 16b which is adapted to receive an expandable diffuser member 128, such as a balloon, that is affixed onto rib 16b. In the alternative, diffuser member 128 may be affixed over rib 65 if a larger diffuser is required. The lipid solution passing through tube 122, passageway 124, and outlet 126 expands diffuser 128 to a desired size. A syringe (not shown) is used to provide the diffuser fluid to tube 122. As best shown in FIG. 4, tube 124 is press-fit onto a rigid tube 130 formed integral with head 12.

Of course, the present invention may be used for invasive photodynamic therapy or other invasive procedures without diffuser 128. Indeed, the diffuser may be totally unnecessary in view of the symmetrical layout of the LED arrays on head 12.

The present invention may also be used for topical and non-invasive treatments by providing a removable reflector 132 (FIG. 2) affixed to support member 16. Reflector 132 has a reflective surface 134 that deflects light from the side-facing LED arrays into substantially parallel rays 136, as depicted in FIG. 2. For invasive procedures, reflector 132 is removed, and the apparatus is used either with diffuser 128 (FIG. 1) or without the diffuser.

Another feature of the present invention is that power to the LED array may be varied in a continuous manner to increase or decrease the total output of the array. This is achieved by the circuit depicted in FIG. 10. In FIG. 10, a potentiometer 136 is used to set the desired power level. Potentiometer 136 provides a reference signal to the positive input of an operational amplifier 138. The negative input of amplifier 138 receives a feedback signal via line 140 from a power transistor 142. The base of transistor 142 is controlled by the output of operational amplifier 138 through a resistor 144. A 12-volt reference 146 provides power to potentiometer 136 through a resistor 148.

In operation, a desired power level is set by the operator on potentiometer 136. The actual power being supplied to the LED arrays is fed back to operational amplifier 138 via line 140. The output of amplifier 138 controls the gating of power transistor 142 so that power being provided to the LED arrays corresponds to the setting of potentiometer 136.

The actual electronic devices in the present invention are preferably substantially monochromatic light emitting diodes that output light energy of a wavelength between about 300 nanometers and 1300 nanometers. The wavelength of the optoelectronic devices is selected based upon the particular photosensitive dye that is used during the photodynamic therapy.

If the invention is to be used in an invasive PDT procedure, the patient may be injected with a photosensitive dye 24 to 72 hours before the procedure. The photosensitive dye tends to collect in malignant cells. However, the present invention may be used in other ways to irradiate a patient or other living cells.

A preferred application for the present invention is the destruction of malignant brain tumors. In this procedure, the surgeon creates an opening in the cranium, and may remove portions of the malignant tumor. However, it may not be necessary to remove portions of the tumor if the output wavelength of the LEDs is sufficiently long and the total power output is sufficiently high to permit relatively deep penetration of the tumor by the light. In any event, the catheter is inserted into the cranial opening, and then into or adjacent to the malignancy. Power is then provided to the catheter head and to the LEDs, thereby activating the photosensitive dye. The activated dye then destroys the malignant cells, as discussed above.

If the invention is to be used for a topical PDT treatment of a skin lesion, cutaneous tumor, or a subcutaneous tumor, or to irradiate a plant, the reflector is placed over the head, and the head is placed over the desired site. Power is then applied to the LEDs to activate the photosensitive dye.

Although several embodiments of the present invention have been shown and described, alternate embodiments will be apparent to those skilled in the art and are within the intended scope of the present invention. Therefore, the invention is to be limited only by the following claims.

We claim:

1. Apparatus used in photodynamic therapy to provide radiant energy to living cells, comprising:
   a thermally-conductive support member having a proximal end;
   a radiation transmitting head interconnected with said proximal end, said head including:
      at least three side faces arranged to encircle said proximal end;
      a substantially non-electrically conductive layer disposed on each of said faces;
      a plurality of optoelectronic devices on each of said layers such that radiant energy may be provided by said devices in a 360 degree arc around said head;
   means for limiting the surface temperature of said head, including
      a first passageway in said support member that receives and carries a cooling fluid to said head; and
      a second passageway in said support member that carries said cooling fluid away from said head.

2. The apparatus of claim 1, wherein said support member comprises an elongated rigid member.

3. The apparatus of claim 1, wherein said head includes an array of light emitting diodes on each of said faces.

4. The apparatus of claim 3, wherein each of said arrays includes a plurality of optoelectronic devices connected in parallel, and wherein said arrays are connected in series to each other.

5. The apparatus of claim 1, wherein said surface temperature limiting means further comprises:
   a temperature sensor that senses the surface temperature of said head; and
   means for reducing the electrical power to said optoelectronic devices if said sensed temperature exceeds a set level.

6. The apparatus of claim 1, further comprising:
   a continuously-variable power source that supplies electrical power to said optoelectronic devices.

7. The apparatus of claim 1, wherein said optoelectronic devices emit substantially monochromatic light having a wavelength of between 300 and 1300 nanometers.

8. The apparatus of claim 1, further comprising:
   a removable reflector disposed around said head.

9. The apparatus of claim 1, further comprising:
   a temperature sensor, mounted to said head, that senses the surface temperature of said head.

10. The apparatus of claim 1, wherein each of said faces is a flat surface.

11. The apparatus of claim 1, wherein said head further comprises:
   an end face;
   a substantially non-electrically conductive layer disposed on said end face; and
   a plurality of optoelectronic devices on said end face layer.

12. A radiation-transmitting head used in photodynamic therapy to provide radiant energy to living cells, said head comprising:

a substantially closed thermally-conductive substrate having at least three side faces arranged to encircle said head;

a substantially non-electrically conductive layer disposed on each of said faces;

a plurality of optoelectronic devices disposed on each of said layers such that radiant energy may be provided by said devices in a 360 degree arc around said head;

a cooling system, including
- a first passageway in said head that receives and carries a cooling fluid to said head; and
- a second passageway in said head that carries said cooling fluid away from said head.

13. The head of claim 12, wherein each of said devices emits substantially monochromatic light having a wavelength of between 300 to 1300 nanometers.

14. The head of claim 12, wherein each of said devices is a substantially monochromatic light emitting diode.

15. The head of claim 12, wherein said substrate has at least eight side faces and an end face, and wherein an array of optoelectronic devices is disposed on each of said side faces and on said end face.

16. The head of claim 12, wherein each of said pluralities of optoelectronic devices includes devices connected in parallel, and wherein said pluralities are connected in series to each other.

17. The apparatus of claim 12, wherein each of said faces is a flat surface.

18. The head of claim 12, further comprising:

an end face;

a substantially non-electrically conductive layer disposed on said end face; and a plurality of optoelectronic devices on said end face layer.

* * * * *